United States Patent
Oshiman et al.

(10) Patent No.: US 7,655,456 B2
(45) Date of Patent: Feb. 2, 2010

(54) ANALYTICAL DEVICE HAVING TEMPERATURE DETECTION UNIT

(75) Inventors: Eisaku Oshiman, Kyoto (JP); Yasunori Shiraki, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 482 days.

(21) Appl. No.: 10/501,797

(22) PCT Filed: Jan. 14, 2003

(86) PCT No.: PCT/JP03/00225

§ 371 (c)(1),
(2), (4) Date: Jul. 15, 2004

(87) PCT Pub. No.: WO03/062812

PCT Pub. Date: Jul. 31, 2003

(65) Prior Publication Data

US 2005/0019219 A1  Jan. 27, 2005

(30) Foreign Application Priority Data

Jan. 18, 2002  (JP)  .............................. 2002-009996

(51) Int. Cl.
C12M 1/34 (2006.01)
C12M 3/00 (2006.01)
G01J 5/00 (2006.01)
G01K 1/16 (2006.01)

(52) U.S. Cl. .................... 435/287.1; 374/120; 374/121; 374/132

(58) Field of Classification Search .............. 435/287.1; 374/120, 121, 132
See application file for complete search history.

(56) References Cited

U.S. PATENT DOCUMENTS

| | | | | |
|---|---|---|---|---|
| 5,320,732 A | * | 6/1994 | Nankai et al. | 204/403.04 |
| 5,405,511 A | * | 4/1995 | White et al. | 205/777.5 |
| 6,066,243 A | | 5/2000 | Anderson et al. | |
| 6,290,838 B1 | * | 9/2001 | Mifsud et al. | 205/775 |
| 6,576,117 B1 | | 6/2003 | Iketaki et al. | |
| 6,766,817 B2 | | 7/2004 | Da Silva | |
| 6,780,296 B1 | * | 8/2004 | Bhullar et al. | 204/403.01 |

(Continued)

FOREIGN PATENT DOCUMENTS

DE  199 52 215  5/2001

(Continued)

*Primary Examiner*—Walter D Griffin
*Assistant Examiner*—Lydia Edwards
(74) *Attorney, Agent, or Firm*—Hamre, Schumann, Mueller & Larson, P.C.

(57) ABSTRACT

The present invention relates to an analytical device (X1) including a mounting portion (10) for mounting an analytical tool (2) capable of outputting information for computation, a computation unit for conducting computation for analyzing a sample based on the information for computation, and a temperature detection unit (12) for outputting the temperature information. The temperature detection unit (12) is disposed in the mounting portion (10). The analytical device (X1) preferably further includes a temperature correction unit for correcting the computation results obtained in the computation unit, based on the temperature information. The temperature detection unit (12) includes, for example, a contact type temperature sensor (12A). In this case, the contact type temperature detection unit (12) may include a thermally conductive portion (12B) having a contact surface (12b) to be brought into contact with the temperature sensor (12A) and the analytical tool (2).

17 Claims, 4 Drawing Sheets

U.S. PATENT DOCUMENTS

| | | |
|---|---|---|
| 6,880,968 B1 | 4/2005 | Haar |
| 2002/0014409 A1* | 2/2002 | Matsumoto et al. ......... 204/403 |
| 2002/0037238 A1 | 3/2002 | Haar et al. |

FOREIGN PATENT DOCUMENTS

| | | |
|---|---|---|
| DE | 100 32 015 | 1/2002 |
| EP | 1 114 994 | 7/2001 |
| JP | 5-126792 | 5/1993 |
| JP | 05126792 A * | 5/1993 |
| JP | 8-10208 | 1/1996 |
| JP | 8-503304 | 4/1996 |
| JP | 2000-19146 | 1/2000 |
| JP | 2001-194334 | 7/2001 |
| JP | 2001-235444 | 8/2001 |
| JP | 2002-48787 | 2/2002 |
| JP | 2002-50205 | 2/2002 |
| WO | WO 85/02257 | 5/1985 |
| WO | WO 99/45375 | 9/1999 |
| WO | WO 99/60391 | 11/1999 |

* cited by examiner

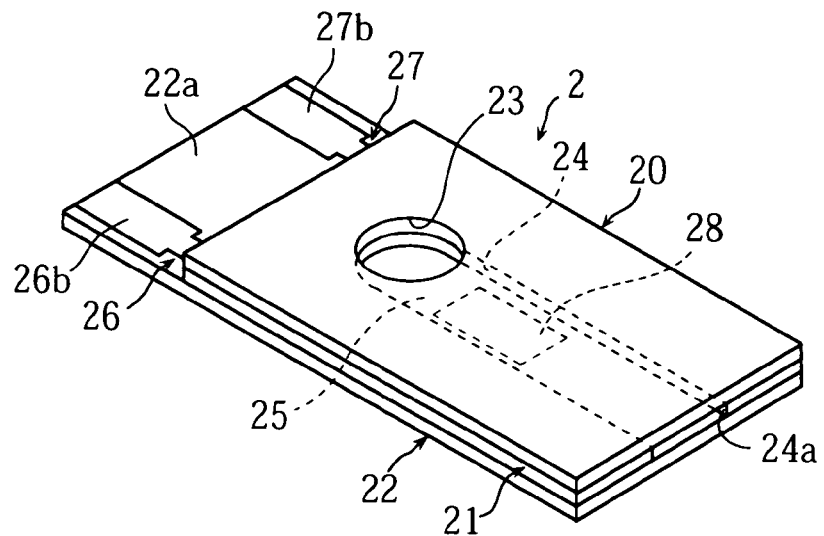
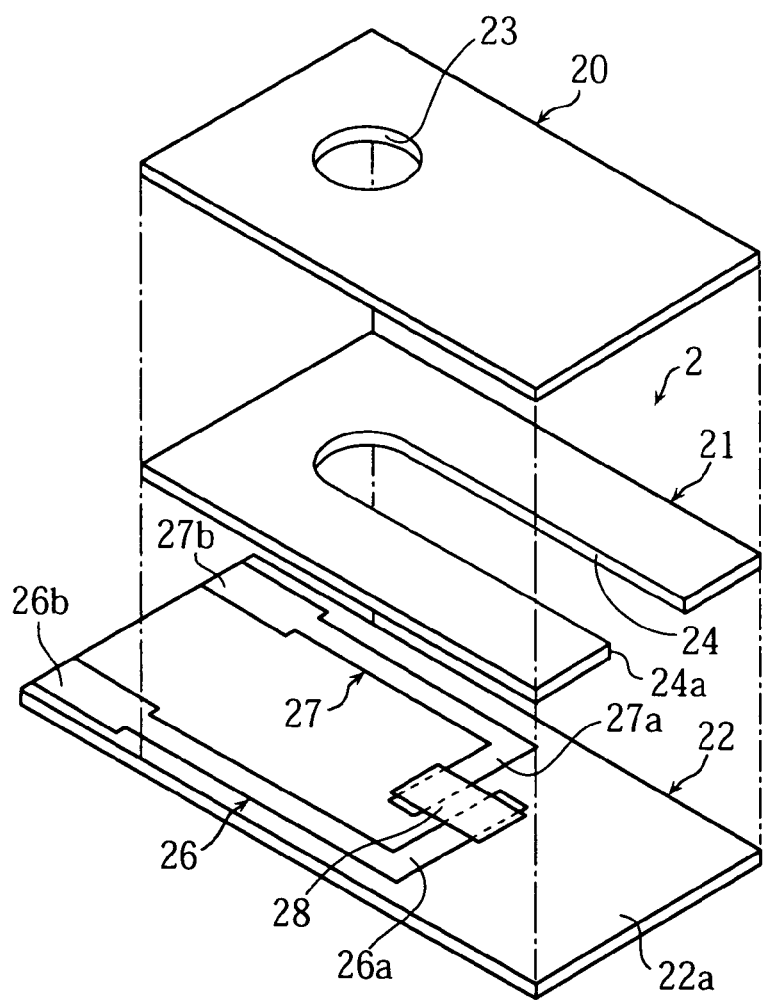

| Concentration \ Temperature | ... | 11~15 | 16~20 | 21~25 | 26~30 | ... |
|---|---|---|---|---|---|---|
| ⋮ | | | | | | |
| 80~90 | | 1.15 | 1.10 | 1.00 | 0.95 | |
| 91~100 | | 1.10 | 1.05 | 1.00 | 0.95 | |
| 101~110 | | 1.10 | 1.05 | 1.00 | 0.95 | |
| 111~120 | | 1.05 | 1.05 | 1.00 | 0.90 | |
| ⋮ | | | | | | |

ANALYTICAL DEVICE HAVING TEMPERATURE DETECTION UNIT

TECHNICAL FIELD

The present invention relates to an analytical device using an analytical tool such as a biosensor installed thereon and conducting analysis of a sample based on the information for computation which is outputted from the analytical tool.

BACKGROUND ART

A redox reaction using an oxidoreductase as a catalyst is known as a general method for measuring a specified component in a sample, for example, the glucose level in blood. On the other hand, personal blood glucose level measuring devices of a size such that they can be held in the palm of the hand have been used to determine the blood glucose level in a simple manner at home or on the trip. In such personal blood glucose level measuring devices, the measurements of blood glucose level are conducted, for example, by mounting a disposable biosensor which is employed for providing an enzyme reaction field in the device and then supplying blood into the biosensor (for example, see JP-B 8-10208).

In the biosensor, a reduction product (or oxidation product) is produced in the amount corresponding to the blood glucose level in the enzyme reaction field. At this time, if a voltage is applied to the enzyme reaction field via electrodes, an electron exchange proceeds between the reduction product (or oxidation product) and the electrode. The quantity of this electron exchange is measured as an oxidation current (or reduction current) in the personal blood glucose level measuring device, and the blood glucose level is computed based on the resulting current.

Because the reaction rate in the enzyme reaction is comparatively strongly depends on temperature, the amount of the produced reduction product (or oxidation product) is easily affected not only by the blood glucose level, but also by the reaction temperature. For this reason, some personal blood glucose level measuring devices were constructed so that the final measurement results were calculated after making a correction for temperature. Temperature measurements in this case are conducted by measuring the internal temperature of the blood glucose level measuring device, for example, with a temperature sensor incorporated in the blood glucose level measuring device. On the other hand, temperature correction can be also conducted by incorporating a temperature sensor in a biosensor and supplying the temperature information from the biosensor to the blood glucose level measuring device.

However, the method for measuring the temperature inside the blood glucose level measuring device does not measure the temperature (reaction temperature) of the biosensor. Therefore, the results obtained do not necessarily reflect the reaction temperature. On the other hand, with the method in which the biosensor is provided with the temperature sensor, the biosensor temperature can be adequately determined, but a temperature sensor has to be provided for each biosensor, thereby making the biosensor more expensive. Therefore, when a disposable biosensor is constructed, it is impractical to provide the biosensor with a temperature sensor. This is why it is necessary to modify the configuration of not only biosensors but also personal blood glucose level measuring devices. For example, it is necessary to provide a personal blood glucose level measuring device with an input unit for receiving temperature information from the biosensor.

DISCLOSURE OF THE INVENTION

It is an object of the present invention to measure adequately the temperature of an analytical tool such as a biosensor, without changing the configuration of the analytical tool, and to compute the concentration by adequately taking into account the effect of the reaction temperature.

The analytical device in accordance with the present invention comprises a mounting portion for mounting an analytical tool capable of outputting information for computation, a computation unit for conducting computation for analyzing a sample based on the information for computation, and a temperature detection unit for outputting the temperature information, wherein the temperature detection is disposed in the mounting portion.

The analytical device in accordance with the present invention preferably further comprises a temperature correction unit for correcting the computation results obtained in the computation unit, based on the temperature information.

The temperature detection unit, for example, comprises a contact type temperature sensor. In this case, the temperature detection unit, for example, comprises a thermally conductive portion having a contact surface to be brought into contact with the temperature sensor and the analytical tool.

The thermally conductive portion is formed, for example, from a material with a thermal conductivity of higher than 0.10 cal/(° C.·cm·sec). Preferably it is formed from a material with a thermal conductivity of higher than 0.15 cal/(° C.·cm·sec). The thermally conductive portion is formed, for example, from iron, copper, aluminum, alloys containing at least one of those metals as the main component, and ceramics.

The contact type temperature sensor and the thermally conductive portion may be disposed in the mounting portion where they are sealed with a resin package. On the other hand, the contact type temperature sensor may be disposed so as to be in direct contact with the analytical tool when the analytical tool is mounted on the mounting portion.

The temperature detection unit may comprise a non-contact type temperature sensor.

The analytical device in accordance with the present invention can use an analytical tool comprising a reagent portion as the analytical tool and can use a disposable analytical tool. The reagent portion, for example, comprises an enzyme. The enzyme, for example, has a catalytic action with respect to the oxidation reaction of glucose. When such an analytical tool is used, the temperature detection unit is preferably disposed so as to be located in the region directly below or in the region directly above the reagent portion when the analytical tool is mounted on the mounting portion.

The mounting portion preferably comprises an insertion portion for inserting the end portion of the analytical tool and a table portion for installing the analytical tool. In this case, the temperature detection unit is disposed in the table portion. The table portion is former, for example, so as to protrude to the side of the analytical device.

A push-down portion for pushing the analytical tool down with respect to the table portion is preferably disposed in the mounting portion. When an analytical tool comprising an output unit for outputting the information for computation is used as the analytical tool, the push-down portion preferably has a capability of being brought into contact with the output unit when the analytical tool is mounted and of inputting the information for computing to the analytical device. In this case, the push-down portion is, for example, a plate spring formed from a conductor.

BRIEF DESCRIPTION OF THE DRAWINGS

FIG. 3 is a full perspective view illustrating an example of the biosensor.

FIG. 4 is an exploded perspective view of the biosensor shown in FIG. 3.

BEST MODE FOR CARRYING OUT THE INVENTION

The best mode for carrying out the present invention will be described hereinbelow in greater detail with reference to the appended drawings.

The first embodiment of the present invention will be initially described with reference to FIG. 1 to FIG. 6.

Figure 1:
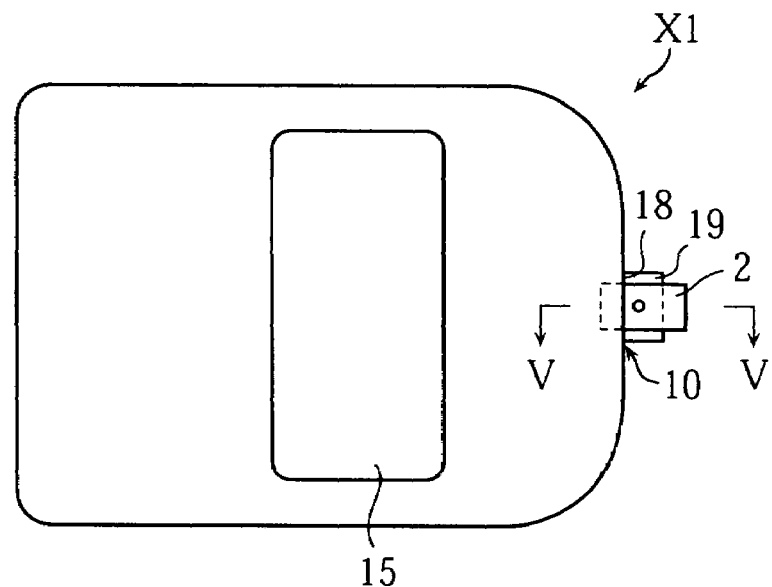
FIG. 1 is a full plan view illustrating the state in which a biosensor is mounted on the analytical device of the first embodiment of the present invention.
Figure 2:
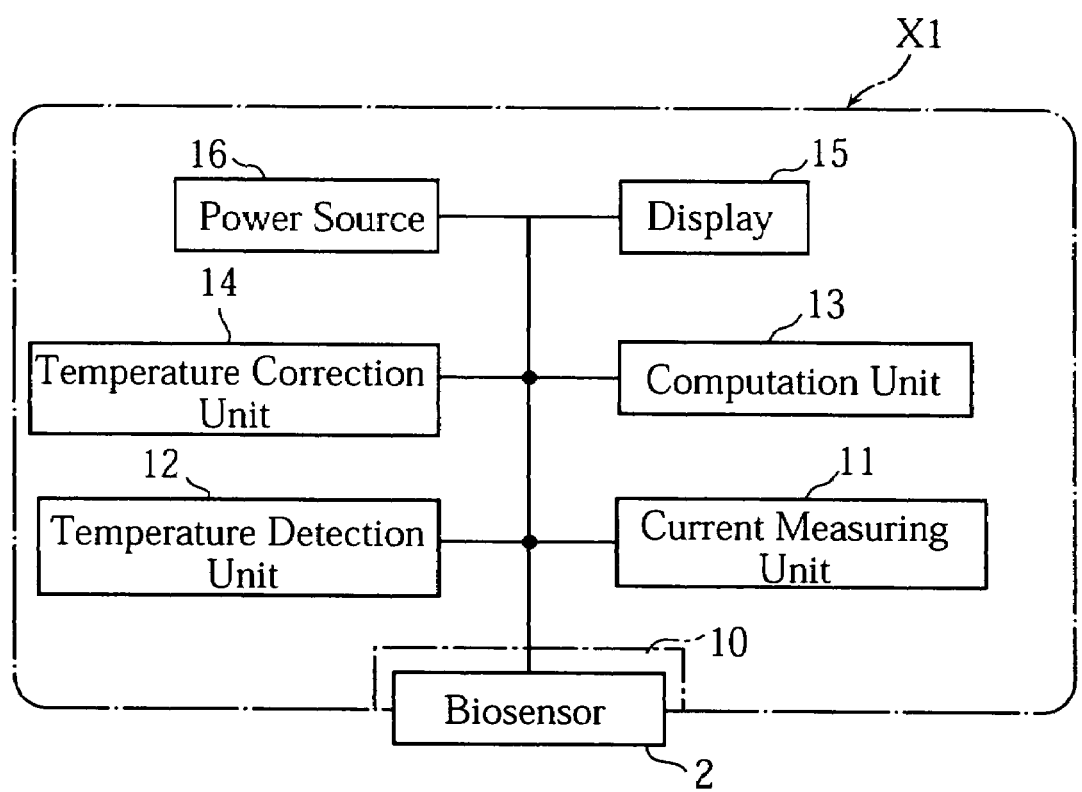
FIG. 2 is a block diagram illustrating a schematic configuration of the analytical device shown in FIG. 1.

As shown in FIG. 1 and FIG. 2, an analytical device X1 comprises a biosensor 2 mounted on a mounting portion 10 and measures the concentration of a specific component in a sample.

Figures 5, 6:
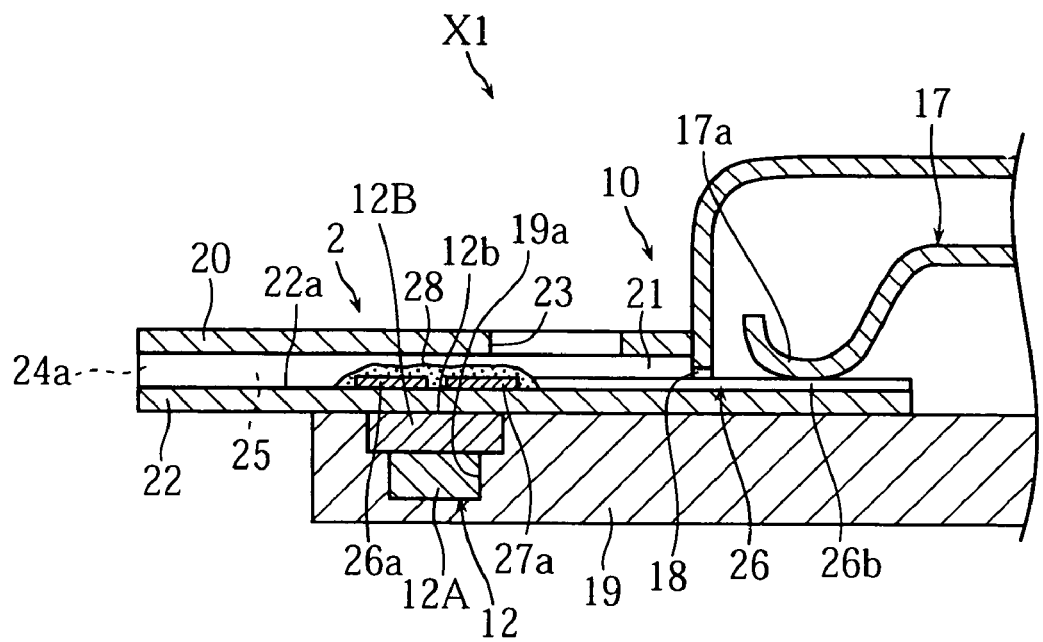
FIG. 5 is a cross-sectional view along the V-V line in FIG. 1.
FIG. 6 is an example of the table of correction coefficients.

The biosensor 2, as shown in FIG. 3 to FIG. 5, comprises a cover 20, a spacer 21, and a substrate 22.

The cover 20 has an orifice 23. The spacer 21 is provided with a slit 24. The slit 24 is designed for setting a flow channel 25 of the biosensor 2, has a distal end opening 24a, and is linked to the orifice 23. Therefore, the flow channel 25 is linked to the outside via the distal end opening 24a and orifice 23. The distal end opening 24a of the cover 20 functions as a sample introduction opening, and the orifice 23 functions as an air release opening. Therefore, when a sample is supplied from the distal end opening (sample introduction opening) 24a, the air present in the flow channel 25 is released to the outside via the orifice 23 and the sample is advanced by a capillary action through the flow channel toward the orifice 23.

A working electrode 26, a counter-electrode 27, and a reagent section 28 are provided at the upper surface 22a of the substrate 22.

The working electrode 26 and counter-electrode 27 extend, in the larger part thereof, in the longitudinal direction of the substrate 22, and the end portions 26a, 27a thereof extend in the lateral direction of the substrate 22. Therefore, the working electrode 26 and counter-electrode 27 as a whole have an L-shaped configuration. The end portions 26b, 27b of the working electrode 26 and counter-electrode 27 are designed for contact with a terminal 17 of the analytical device X1, as shown in detail in FIG. 5. The reagent section 28 has, for example, a rectangular shape and, as shown in detail in FIG. 4 and FIG. 5, connects the end portions 26a, 27a of the working electrode 26 and counter-electrode 27 to each other. The reagent section 28 for example comprises a relatively large quantity of an electron conductive substance having a relatively small quantity of an oxidizing-reducing enzyme dispersed therein.

For example, complexes of iron or Ru can be used as the electron conductive substance. Potassium ferricyanide is an example of an iron complex that can be used in this case. Examples of suitable Ru complexes include those with $NH_3$ as a ligand. The oxidizing-reducing enzyme is selected according to the type of the specific component which is the object of analysis. Examples of specific components include glucose, cholesterol, and lactic acid. Examples of oxidizing-reducing enzymes corresponding to those specific components include glucose dehydrogenase, glucose oxidase, hexokinase, cholesterol dehydrogenase, cholesterol oxidase, lactic acid dehydrogenase, and lactic acid oxidase.

As shown in FIG. 1, FIG. 2, and FIG. 5, in addition to the mounting portion 10, the analytical device X1 comprises a current measuring unit 11, a temperature detection unit 12, a computation unit 13, a temperature correction unit 14, a display 15, a power source 16, and a pair of terminals (one terminal 17 is depicted in FIG. 5).

As shown in FIG. 1 and FIG. 5, the mounting portion 10 is designed for holding the biosensor 2 and comprises an insertion portion 18 and a table portion 19. The insertion portion 18 is designed for inserting the end portion of the biosensor 2. The table portion 19 is designed for installing a biosensor 2 and protrudes to the side of the analytical device X1. A recess 19a for accommodating the temperature detection portion 12 is provided in the table portion. The recess 19a is so provided as to be positioned directly below the reagent portion 28 in the biosensor when the biosensor 2 is mounted on the mounting portion 10.

The current measuring unit 11 is not clearly shown in the figures. It is connected to a pair of terminals and serves to measure the response current when a voltage is applied between the pair of terminals 17.

The temperature detection unit 12 is designed for measuring the temperature of the biosensor. As shown in detail in FIG. 5, this unit is accommodated in the recess 19a of the table portion 19. Therefore, when the biosensor 2 is mounted on the mounting portion, the temperature detection unit is disposed so as to be positioned directly below the reagent portion 28 in the biosensor 2. The temperature detection unit 12 comprises a temperature sensor 12A and a thermally conductive portion 12B. The temperature sensor 12A has a contact type configuration. The thermally conductive portion 12B is formed, for example, from a material with a thermal conductivity of higher than 0.10 cal/(° C.·cm·sec), preferably, from a material with a thermal conductivity of higher than 0.15 cal/(° C.·cm·sec). Examples of such materials include iron, copper, aluminum, alloys containing at least one of those metals as the main component, and ceramics. The thermally conductive portion 12B covers the temperature sensor 12A, while being in contact with the temperature sensor 12A, and is so disposed that the surface 12b thereof is in the same plane with the surface of the table portion 19. Therefore, when the biosensor 2 is mounted on the mounting portion 10, the thermally conductive portion 12B can be in contact with the substrate 22 of the biosensor 2, and the temperature of the biosensor 2 can be measured with the temperature sensor 12A via the thermally conductive portion 12B. Furthermore, because the thermally conductive portion 12B is disposed so that it covers the temperature sensor 12A, the surface of the temperature sensor 12A is protected from damage or adhesion of foreign matter such as dust.

The computation unit 13 shown in FIG. 2 computes the concentration of the specific component in the sample based on the measurement results of the current measuring unit 11. The computation of concentration is carried out, for example, by fitting the measured current in a calibration curve representing the relationship between a current and a concentration. The calibration curve may be also specified as a relationship between a voltage and a concentration. In this case, the computation of concentration can be conducted by converting the measured current into a voltage based on the same rule and fitting the voltage in the calibration curve.

The temperature correction unit corrects the computation results obtained in the computation unit 13 according to the temperature information from the temperature detection unit 12. The temperature correction unit 14, for example, stores data relating to a table of correction coefficients. An example of such a table is shown in FIG. 6. The table is so compiled that the correction coefficients can be calculated from combinations of temperature and computed concentration considered as parameters. In the temperature correction unit 14 shown in FIG. 2, the final concentration after temperature correction taking the reaction temperature into account is determined by multiplying the computation results obtained in the computation unit 13 by the selected correction coefficients. The aforementioned table is not limited to that shown in FIG. 6. For example, segments of temperature or concentration can be changed. The correction coefficients are also not limited to the values shown in FIG. 6.

Each of the computation unit 13 and temperature correction unit 14 shown in FIG. 2 can be composed, for example, of a CPU, a RAM, and a ROM, but both the computation unit 13 and temperature correction unit may be also constructed by connecting a plurality of memories such as RAM and ROM to one CPU.

The display unit 15 shown in FIG. 1 and FIG. 2 is designed to display not only the computation results obtained with the temperature correction unit 14, but also error messages and the like. It is composed, for example, of a LCD.

The power source 16 shown in FIG. 2 is used for supplying electric power to units 11-15 or for applying a voltage between a pair of terminals 17. The power source 16 is composed, for example, of a DC power source such as a dry battery or rechargeable battery.

As shown in FIG. 5, the terminals 17 are used when a voltage is applied between the working electrode 26 and counter-electrode 27 of the biosensor 2 or when the electron exchange amount between the working electrode 26 and the electron conductive substance is measured. For this purpose the terminals 17 are so disposed that the distal end portion 17a thereof is brought into contact with end portions 26b, 27b of the working electrode 26 and counter electrode 27 of the biosensor 2 when the biosensor 2 is mounted on the mounting portion 10. Each terminal is constructed as a plate spring with a bent conductor tab. Therefore, when the biosensor 2 is mounted on the mounting portion 10, the distal end portion 17a of the terminal 17 is brought into contact with the end portions 26b, 27b, while applying a push-down pressure to the end portions 26b, 27b of the working electrode 26 and counter-electrode 27. As a result, the biosensor is strongly attached to the table portion 19 and, therefore, to the temperature detection unit 12.

The concentration measurement operation in the analytical device X1 will be described below.

In the analytical device X1, first, a decision is made as to whether the biosensor 2 has been mounted. If the biosensor 2 has been mounted, the working electrode 26 and counter-electrode 27 are brought into contact with the terminal 17, as shown in greater detail in FIG. 5, and an electric current can be measured in the current measuring unit 11. Therefore, a decision as to whether the biosensor 2 has been mounted can be made, for example, based on the current measured in the current measuring unit 11. A decision as to whether the biosensor 2 has been mounted may be also made by using an optical sensor or a pressure sensor.

When the mounting of the biosensor 2 on the analytical device X1 has been confirmed, the supply of the sample to the reagent portion 28 is confirmed. This confirmation can be made based on the electric current measured in the current measuring unit 11. More specifically, it can be made by checking as to whether the current measured in the current measuring unit 11 has reached the predetermined threshold. The reagent portion 28 is dissolved by the supply of the sample, and a liquid-phase reaction system is created in the flow channel 25. In the liquid-phase reaction system, the specific component present in the sample is oxidized (or reduced), and the electron conductive substance is reduced (or oxidized). As a result, if a voltage exceeding a preset value is applied between the working electrode 26 and counter-electrode 27, the electron conductive substance that was subjected to reduction (oxidation) is oxidized (or reduced), thereby generating an oxidation current (or reduction current). Therefore, measuring the oxidation current (or reduction current) in the current measuring unit 11 makes it possible to confirm that the adequate reaction proceeds in the liquid-phase reaction system. As a result, the supply of the sample to the reagent portion 28 can be confirmed.

Once the supply of the sample has been confirmed, the application of voltage between the working electrode 26 and counter-electrode 27 is terminated. As a result, the reduced (or oxidized) electron conductive substance is accumulated in the liquid-phase reaction system (flow channel 25). Once a prescribed interval has elapsed after the termination of voltage application, a voltage is again applied between the working electrode 26 and counter-electrode 27. As a result, the electron conductive substance is oxidized (or reduced). Therefore, electron exchange is conducted between the liquid-phase reaction system and the working electrode 26 and the response current can be measured in the current measuring unit 11.

Once a prescribed interval has elapsed after the confirmation of sample supply, the response current measured by the current measuring unit 11 is acquired and employed as a basis for computations in the computation unit 13. However, the application of voltage between the working electrode 26 and counter-electrode 27 is still continued even after the supply of the sample to the reagent portion 28 has been confirmed, and the response current measured by the current measuring unit 11 when a prescribed interval has elapsed since the confirmation of sample supply is employed as a basis for computations in the computation unit 13.

On the other hand, the temperature correction unit 14 determines the correction coefficients based on the temperature information from the temperature detection unit 12 and computation results from the computation unit 13, and those correction coefficients are multiplied by the computation results obtained in the computation unit 13 to determine the final concentration.

In the present embodiment, the temperature detection unit 12 was provided in the mounting portion 10 in the analytical device X1 to measure the temperature of the biosensor 2.

Therefore, when the temperature of the biosensor 2 is measured, it is not necessary to provide the biosensor 2 with the temperature detection function of a temperature sensor or the like, this feature being beneficial in terms of production cost of the biosensor 2. Further, though the temperature detection unit 12 was provided in the analytical device X1, this temperature detection unit 12 is designed for measuring the temperature of the biosensor 2, rather than the temperature inside the analytical device X1. In particular, if the temperature detection unit 12 is disposed in the vicinity of the biosensor 2, the temperature measured by the temperature detection unit 12 is approximated by the temperature of the biosensor 2. Further, if the temperature detection unit 12 is provided so as to be located in the region directly below the reagent portion 28 or in the vicinity thereof, then the temperature measured by the temperature detection unit 12 is approximated by the reaction temperature and the reaction temperature can be adequately determined. As a result, the concentration computation can be conducted with good accuracy by taking the reaction temperature into account.

Figure 7:
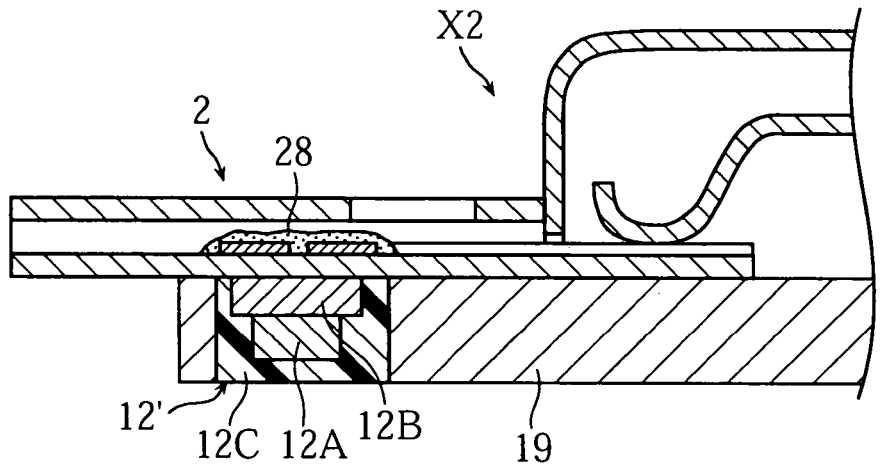
FIG. 7 is a cross-sectional view of the main portion illustrating the state in which a biosensor is mounted on the analytical device of the second embodiment of the present invention; this view corresponds to the cross section along the V-V line in FIG. 1.
Figure 8:
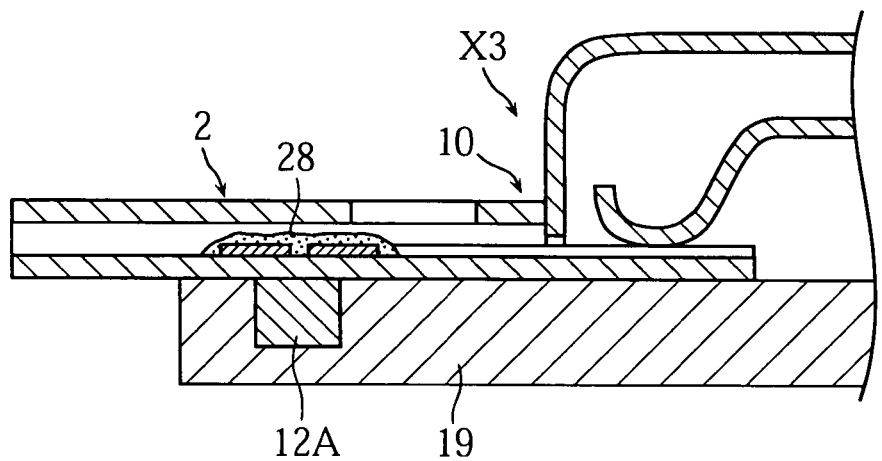
FIG. 8 is a cross-sectional view of the main portion illustrating the state in which a biosensor is mounted on the analytical device of the third embodiment of the present invention; this view corresponds to the cross section along the V-V line in FIG. 1.
Figure 9:
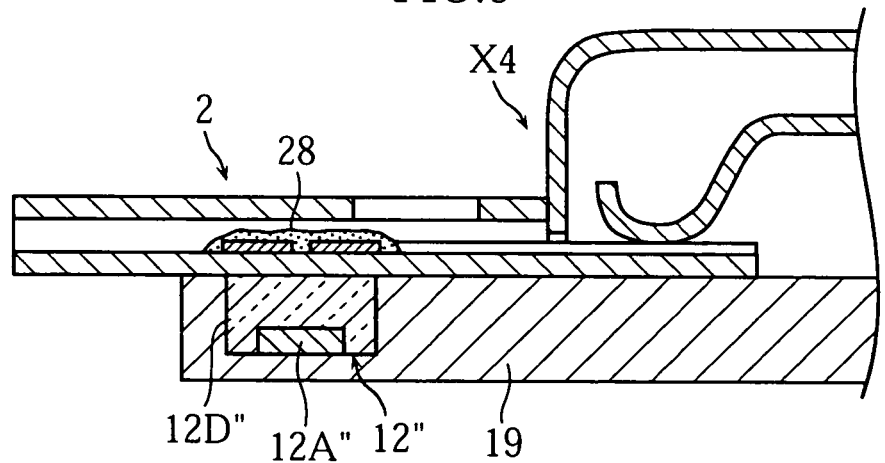
FIG. 9 is a cross-sectional view of the main portion illustrating the state in which a biosensor is mounted on the analytical device of the fourth embodiment of the present invention; this view corresponds to the cross section along the V-V line in FIG. 1.

The second, third and fourth embodiments of the present invention will be described hereinbelow with reference to FIG. 7 to FIG. 9. In FIG. 7 to FIG. 9, the elements identical to those of the above-described first embodiment of the present invention are assigned with the same reference numerals and redundant explanation thereof is herein omitted.

As shown in FIG. 7, the configuration of the temperature detection unit 12' in the analytical device X2 of the second embodiment is different from that in the analytical device X1 (see FIG. 5) relating to the above-described embodiment. In the temperature detection unit 12', the temperature sensor 12A and thermally conductive portion 12B are sealed with a resin package 12C to obtain a module, and this module is fit into the table portion 19.

As shown in FIG. 8, in the analytical device X3 of the third embodiment, the temperature detection unit is composed only of the temperature sensor 12A. The temperature sensor 12A is so disposed that the surface thereof exposed in the table portion 19. As a result, when the biosensor 2 is mounted on the mounting portion 10, the temperature sensor 12A is brought into direct contact with the biosensor 2.

As shown in FIG. 9, the analytical device X4 of the fourth embodiment uses a non-contact sensor as the temperature sensor 12A". The temperature detection unit 12" further comprises a transparent element 12D". As a result, damage of the surface of the temperature sensor 12A" can be inhibited and the adhesion of foreign matter to the surface of the temperature sensor 12A" can be inhibited.

The present invention is not limited to the above-described first to fourth embodiment, and various design modifications can be used. Thus, the temperature detection units 12, 12', 12" may be disposed in any region (mounting portion) where the temperature of the biosensor 2 can be adequately measured, and not necessarily in the region directly below the reagent portion 28. The analytical device X1 comprises the temperature correction unit 14, but this temperature correction unit 14 is not a mandatory component and can be omitted. For example, the biosensor temperature can be displayed on the display based on the information from the temperature detection unit in the analytical device, but a correction table (for example, the table shown in FIG. 6) can be prepared in advance separately from the analytical device, and the user himself can correct the actually measured value based on the displayed temperature and the correction table.

The invention claimed is:

1. A combination of an analytical tool and a temperature detecting analytical device, the temperature detecting analytical device comprising a housing including a mounting portion for mounting the analytical tool capable of outputting information for computation, a computation unit for conducting computation for analyzing a sample based on said information for computation, and a temperature detection unit for outputting temperature information, wherein said mounting portion comprises a table having a projecting portion protruding from said housing;

wherein said analytical tool comprises a substrate separate from said mounting portion and a reagent portion formed on said substrate, said reagent portion being located above said projecting portion of said table outside said housing when said analytical tool is mounted onto said mounting portion; and wherein said temperature detection unit is located on said projecting portion of said table directly below and in vertical alignment with said reagent portion when said analytical tool is mounted on said mounting portion.

2. The combination according to claim 1, wherein the temperature detecting analytical device further comprises a temperature correction unit for correcting the computation results obtained in said computation unit, based on said temperature information.

3. The combination according to claim 1, wherein said temperature detection unit comprises a contact type temperature sensor.

4. The combination according to claim 3, wherein said temperature detection unit comprises a thermally conductive portion having a contact surface for contact with said temperature sensor and said analytical tool.

5. The combination according to claim 4, wherein said thermally conductive portion is formed of a material with a thermal conductivity of higher than 0.10 cal/(° C.·cm·sec).

6. The combination according to claim 5, wherein said thermally conductive portion is formed of a material with a thermal conductivity of higher than 0.15 cal/(° C.·cm·sec).

7. The combination according to claim 4, wherein said temperature sensor and said thermally conductive portion are scaled wit a resin package in said projecting portion of said table.

8. The combination according to claim 3, wherein said temperature detection unit comprises a contact type temperature sensor, and the temperature sensor is disposed in direct contact with said analytical tool when said analytical tool is mounted on said mounting portion.

9. The combination according to claim 1, wherein said temperature detection unit comprises a non-contact type temperature sensor.

10. The combination according to claim 1, wherein said reagent portion comprises an enzyme.

11. The combination according to claim 10, wherein said enzyme has a catalytic action with respect to oxidation reaction of glucose.

12. The combination according to claim 1, wherein said analytical tool is disposable.

13. The combination according to claim 1, wherein said mounting portion comprises an insertion portion for inserting an end portion of said analytical tool.

14. The combination according to claim 13, further comprising a push-down portion disposed in said housing for pushing down said analytical tool against said table portion.

15. The combination according to claim 14, wherein said analytical tool comprises an output unit for outputting said information for computation, said push-down portion being brought into contact with said output unit and inputting said information for computing.

16. The combination according to claim 15, wherein said push-down portion is an electrically conductive plate spring.

17. The combination according to claim 1, wherein the housing includes an insertion opening directly above the table, the analytical tool further includes a cover formed over the substrate, the substrate extending beyond the cover for insertion into the insertion opening, the cover coming into stopping contact with the housing upon insertion of the substrate into the insertion opening for positioning said temperature detection unit directly below and in vertical alignment with said reagent portion.

* * * * *

UNITED STATES PATENT AND TRADEMARK OFFICE
CERTIFICATE OF CORRECTION

PATENT NO. : 7,655,456 B2  Page 1 of 1
APPLICATION NO. : 10/501797
DATED : February 2, 2010
INVENTOR(S) : Oshiman et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 925 days.

Signed and Sealed this

Twenty-third Day of November, 2010

David J. Kappos
*Director of the United States Patent and Trademark Office*